United States Patent [19]
Baker et al.

[11] 4,267,191
[45] May 12, 1981

[54] PROCESS FOR ENHANCING GROWTH PROMOTION IN ANIMALS

[75] Inventors: Pamela K. Baker, Hopewell; Goro Asato, Titusville; John Dusza, Nanuet, all of N.J.

[73] Assignee: American Cyanamid Company, Stamford, Conn.

[21] Appl. No.: 152,267

[22] Filed: May 21, 1980

[51] Int. Cl.³ .............................................. A61K 31/44
[52] U.S. Cl. .................................................... 424/285
[58] Field of Search ........................................ 424/285

[56] References Cited

U.S. PATENT DOCUMENTS 4,051,258  9/1977  Durr et al. ............................ 424/285

Primary Examiner—Frederick E. Waddell
Attorney, Agent, or Firm—Harry H. Kline

[57] ABSTRACT

There are provided novel furfuryl thiourea compounds which are effective for enhancing the growth rate of meat-producing animals and for improving the efficiency of feed utilization thereby, when administered to said animals in effective amounts in or with their feed or by parenteral administration.

10 Claims, No Drawings

PROCESS FOR ENHANCING GROWTH PROMOTION IN ANIMALS

The present invention relates to novel furfuryl thiourea compounds. More particularly, it relates to methods for preparing the same and furfuryl thiourea compounds having the structure:

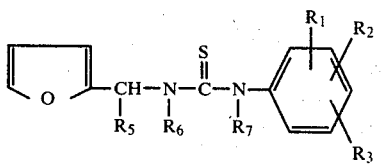

wherein $R_1$ is hydrogen, halogen, alkyl $C_1$-$C_4$, alkoxy $C_1$-$C_4$, $CF_3$, alkylthio $C_1$-$C_4$, nitro, cyano, $C_1$-$C_4$ alkanoyl, —$COOR_4$ or

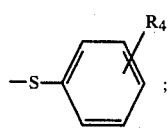

$R_2$ and $R_3$ are each selected from the group consisting of hydrogen, halogen, alkyl $C_1$-$C_4$ and alkoxy $C_1$-$C_4$; $R_4$ is hydrogen or alkyl $C_1$-$C_4$; $R_5$, $R_6$ and $R_7$ are each hydrogen or alkyl $C_1$-$C_4$, preferably methyl; with the proviso that when two of said $R_1$, $R_2$ and $R_3$, are hydrogen, the remaining R group cannot be hydrogen, chloro, methyl or methoxy. Still more particularly, the invention is concerned with a method for enhancing the growth rate of animals and improving the efficiency of feed utilization thereby, by orally or parenterally administering to said animals an effective amount of the furfuryl thiourea compound hereinabove identified.

It has been surprisingly found that meat animals' feed efficiency can be markedly improved by orally administering to said animals in or with the feed an amount of furfuryl thiourea compound equivalent to between 0.0001% to 1.00% (1–10,000 ppm). The preferred amount for poultry for instance is 0.0001% to 0.01% (1–100 ppm); for cattle and sheep for instance, the preferred amount is 0.0001% to 0.1% (1–1000 ppm); and for swine for example, the preferred amount is 0.0001% to 0.05% (1–500 ppm) by weight of feed.

In practice, the furfuryl thiourea compound is generally formulated as a premix and/or animal feed supplement which is admixed with a nutritionally balanced feed or added to the feed as a top dressing, or the like. Premixes may be blending about 70% to 95% by weight of an edible diluent such as soybean meal, ground corn, ground rice hulls, rice flour, or the like, with about 1% to 30% by weight of the active furfuryl thiourea compound.

The growth rate of animals is also improved when a furfuryl thiourea as defined above is administered as a subcutaneous implant under the skin of the animal. Implants are generally in the form of a paste or pellet which permits the active compound to be released into the bloodstream of the animal over an extended period of time, as for example, from several weeks to several months.

Whether the implant is in the form of a paste or pettet is a matter of choice. Pettet-type implants which can be used in accordance with this invention may be prepared by admixing from about 50% to 95% by weight of a furfuryl thiourea compound with from about 50% to 5% by weight of a pharmaceutically acceptable carrier, such as Castorwax (i.e., glyceryl 12-hydroxysterate), beeswax, starch, or a high molecular weight (i.e., 4000) polyethylene glycol, or mixtures thereof, along or in combination with a small amount of a lubricant, such as zinc stearate or magnesium stearate. A small amount of polyvinylpyrrolidone and dibutylphthalate may also be incorporated in the above-defined formulations.

Paste implants can be prepared using the same percentages or drug as stated above, but employing a mixture of high molecular weight (i.e., 4000) polyethylene glycol and low molecular weight (i.e., 400) polyethylene glycol alone, or in combination with, Castorwax or beeswax and/or polyvinylpyrrolidone.

In general, implants can vary in size and weight, but usually range between 10 mg and 100 mg per implant. Advantageously, with this method of application, the drug can be administered at periodic intervals throughout the feeding period of the animals. Moreover, formulations and intervals between implantations can be varied to provide a daily drug release of generally about 0.0005 mg to 0.2 mg per kg of body weight, and preferably 0.001 mg to 0.1 mg per kg of body weight.

Typical implant formulations are as follows:

| Typical Pellet Implant Formulations | | |
| --- | --- | --- |
| | | Preferred |
| (A) | 1-Furfuryl-2-Thio-3-(2,6-xylyl urea | 50.0%* |
| | Lubricant (i.e., magnesium stearate) | 0.5%* |
| | Glyceryl 12-Hydroxystearate-QS | |
| (B) | 1-Furfuryl-3-mesityl-2-Thiourea | 60.0% |
| | Polyethylene glycol 4000 | 10.0* |
| | Beeswax-QS | |
| (C) | 1-(2,6-diethylphenyl)-3-furfuryl-2-thiourea | 30.0 mg |
| | Beeswax | 1.0 mg |
| | Magnesium stearate | 1.5 mg |
| | Dibutylphthalate | 1.0 mg |
| | Polyvinylpyrrolidone (10% Solution)-QS | |

| Typical Paste Implant Formulation | | |
| --- | --- | --- |
| | | Preferred |
| (A) | 1-Furfuryl-3-(o-methoxyphenyl)-2-thiourea | 200 mg |
| | Polyethylene glycol 4000 (30% to 50%) | 40%* |
| | Polyethylene glycol 400-QS | |

*Percent by weight

In accordance with this invention, a furfuryl thiourea compound having the structure:

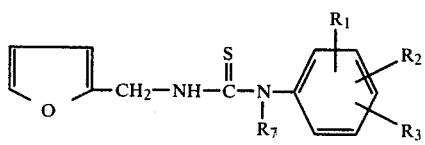

wherein $R_1$ is hydrogen, halogen, alkyl $C_1$-$C_4$, alkoxy $C_1$-$C_4$, $CF_3$, alkylthio $C_1$-$C_4$, nitro, cyano, $C_1$-$C_4$ alkanyol, —$COOR_4$ or

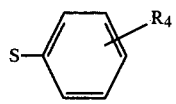

$R_2$ and $R_3$ each represent members selected from hydrogen, halogen alkyl $C_1$–$C_4$ and alkoxy $C_1$–$C_4$; $R_4$ is hydrogen or alkyl $C_1$–$C_4$; and $R_7$ is hydrogen or alkyl $C_1$–$C_4$; can be prepared by reacting furfurylisothiocyanate:

with an equivalent amount of an appropriately substituted aniline having the structure:

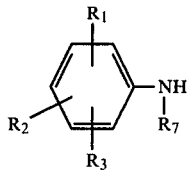

where $R_1$, $R_2$, $R_3$ and $R_7$ are as defined hereinabove, in the presence of an inert organic solvent such as an aromatic hydrocarbon, aliphatic hydrocarbon, chlorinated hydrocarbon, tetrahydrofuran, dioxane, or the like, at a temperature between about 20° and 100° C. Inert solvents, such as hexane, heptane, pentane, benzene, toluene, chloroform, tetrahydrofuran (THF), xylene and the like are illustrative of those which may be employed in this reaction.

The furfurylisothiocyanate intermediate herein can be prepared by reacting furfurylamine with carbon disulfide in the presence of base and treating the thus formed reaction mixture with sodium hypochlorite. This reaction is preferably conducted in the presence of an inert solvent such as methylene chloride at a temperature between about 0° and 10° C.

These reactions may be illustrated as follows:

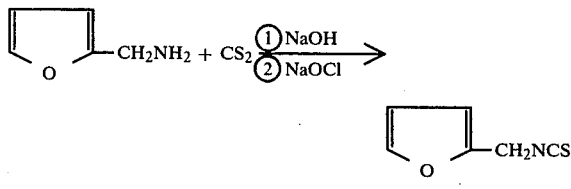

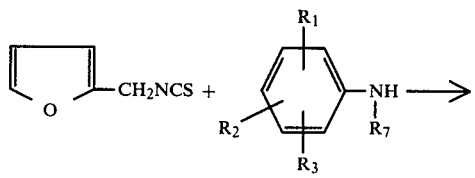

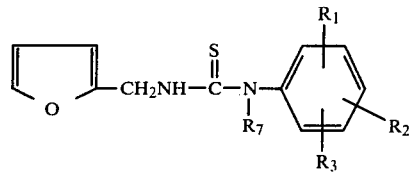

wherein $R_1$, $R_2$, $R_3$ and $R_7$ are as defined above.

The furfuryl thiourea compounds of the present invention may also be prepared by reacting the appropriately substituted phenylisothiocyanate with an equivalent amount of an appropriately substituted furfurylamine. The reaction is preferably conducted in an inert solvent such as hexane, benzene, toluene, or the like, at a temperature between about 20° and 60° C. The reaction may be illustrated as follows:

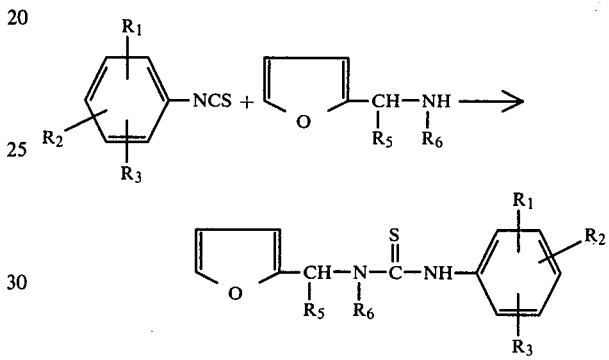

where $R_1$, $R_2$, $R_3$, $R_5$ and $R_6$ are as described above.

A still further embodiment for the preparation of the furfuryl thiourea compounds of the present invention involves the preparation of ammonium furfuryldithiocarbamate by reaction of furfurylamine with carbon disulfide in the presence of aqueous ammonium hydroxide. The furfuryldithiocarbamate is then converted to furfurylisothiocyanate by reaction with aqueous sodium hypochlorite. The thus-prepared furfurylisothiocyanate may then be reacted, as described above, with the appropriate aniline to yield the desired furfuryl thiourea.

The following examples serve to further illustrate the present invention.

EXAMPLE 1

Preparation of 1-Furfuryl-2-thio-3-(2,6-xylyl)urea

A solution of 125.4 g of 2,6-dimethylphenyl isothiocyanate is added dropwise to a mixture of 74.6 g of furfurylamine in 1.5 liters of hexane. The mixture is stirred at room temperature for 16 hours. The solid product is collected by filtration and dried to afford 107.8 g of the title compound, m.p. 102°–105°.

The above procedure is repeated in every detail except that the appropriately substituted phenylisothiocyanate is substituted for 2,6-dimethylphenylisothiocyanate to yield the compounds described below:

| Compound | Melting Point °C. |
| --- | --- |
| 1-(2,6-dichlorophenyl)-3-furfuryl-2-thiourea | 163–167 |
| 1-furfuryl-2-thio-3-(2,3-xylyl)urea | 102–104 |
| 1-furfuryl-3-(o-nitrophenyl)-2-thiourea | 85–89 |
| 1-(2,6-diisopropylphenyl)-3-furfuryl-2- | 130–134 |

-continued

| Compound | Melting Point °C. |
| --- | --- |
| thiourea | |
| 1-furfuryl-3-[o-(methylthio)phenyl]-2-thiourea | 99–102 |
| 1-furfuryl-3-mesityl-2-thiourea | 127–131 |
| 1-(2,6-diethylphenyl)-3-furfuryl-2-thiourea | 84–85 |
| 1-furfuryl-2-thio-3-o-tolylurea | 86–89 |
| 1-furfuryl-2-thio-3-($\alpha,\alpha,\alpha$-trifluoro-o-tolyl)urea | 103–107 |
| 1-(o-fluorophenyl)-3-furfuryl-2-thiourea | 109–113 |
| 1-furfuryl-3-(o-methoxyphenyl)-2-thiourea | 108–111 |
| 1-furfuryl-2-thio-3-[o-(p-tolylthio)phenyl]urea | 80–83 |
| 1-furfuryl-3-(p-nitrophenyl)-2-thiourea | 114–117 |
| 1-furfuryl-2-thio-3-(2,4-xylyl)urea | 120–123 |
| 1-(p-Cyanophenyl)-3-furfuryl-2-thiourea | 156–159 |
| 1-(p-chlorophenyl)-3-furfuryl-2-thiourea | 116–119 |
| 1-furfuryl-2-thio-3-(2,6-xylyl)urea | 125–138 |
| 1-(p-acetylphenyl)-3-furfuryl-2-thiourea | 147–149 |
| 1-furfuryl-2-thio-3-p-tolylurea | 166–169 |
| 1-(o-cyanophenyl)-3-furfuryl-2-thiourea | 169–172 |
| 1-furfuryl-3-(p-methoxyphenyl)-2-thiourea | 110–114 |
| 3-(2,6-dichlorophenyl)-1-furfuryl-1-methyl-2-thiourea | 133–137 |
| 1-(2-ethyl-p-tolyl)-3-furfuryl-2-thiourea | 79–72 |
| 1-furfuryl-1-methyl-2-thio-3-(2,6-xylyl)urea | 130–133 |
| 1-($\alpha$-methylfurfuryl)-2-thio-3-(2,6-xylyl)urea | 138–141 |

EXAMPLE 2

Preparation of 1-Furfuryl-2-thio-3-(2,6-xylyl)urea

Furfurylamine (9.71 g) is added over 30 minutes to a stirred, cooled mixture of 8.84 g of NaOH, 20 ml of $CH_2Cl_2$, 15 ml of $H_2O$ and 7.5 ml of $CS_2$. The mixture is stirred 55 minutes in the ice bath and 600 ml of 5.25% aqueous NaOCl solution is added over 1 hour and 45 minutes (temperature is maintained at 8° C. or less). After stirring 16 hours at 20° C., the reaction mixture is extracted three times with $CH_2Cl_2$ (total volume of combined $CH_2Cl_2$ extracts is 600 ml). The $CH_2Cl_2$ extract is washed with 2×100 ml of $H_2O$, dried with $Na_2SO_4$ and evaporated to give 12.4 g of crude furfurylisothiocyanate.

The crude isothiocyanate is shaken with hexane (2×60 ml) and the hexane-soluble material is added over 10 minutes to a stirred solution of 12.1 g of 2,6-dimethylaniline in hexane (50 ml). After sixteen hours, the white solid is collected, washed with 3×10 ml hexane and air dried to give 10.03 g (38.5% yield) of the desired thiourea having a melting point equal to 103°–106° C.

Employing the appropriately substituted aniline in the above-reaction in place of 2,6-dimethylaniline there is obtained 3-furfuryl-1-methyl-2-thio-1-(2,6-xylyl)urea having a melting point equal to 47.5°–49.5° C.

EXAMPLE 3

Preparation of Ammonium furfuryldithiocarbamate

Furfurylamine (4.85 g) is added dropwise over 50 minutes to a vigorously stirred mixture of 3.75 ml of $CS_2$ and 8.3 ml of 29.7% aqueous ammonia cooled in ice and methyl alcohol. The cooling bath is removed and the thick orange suspension stirred 16 hours more, filtered and air dried to yield 3.11 g (32.7% yield) of desired product characterized by m.p. equal to 88° C. dec.

EXAMPLE 4

Preparation of 1-Furfuryl-2-thio-3-(2,6-xylyl)urea

A 5.25% aqueous NaOCl solution (60 ml) is added to a stirred, cooled suspension of 1.9 g of ammonium furfuryldithiocarbamate in 20 ml of $CH_2Cl_2$ at such a rate that the temperature does not exceed 6° C. The mixture is stirred one hour at 20° C. and extracted with 3×50 ml of $CH_2Cl_2$. The combined extracts are washed with $H_2O$ (2×50 ml) dried ($Na_2SO_2$) and evaporated to afford 1.13 g of (81.2% yield) of crude furfurylisothiocyanate (NMR, IR are supportive of the structure).

The crude isothiocyanate is treated with 6 ml of hexane and the hexane soluble material is added to a stirred solution of 0.98 g of 2,6-dimethylaniline in 5 ml of hexane. After sixteen hours the solid is collected, washed with 2×3 ml of hexane and air dried to give 1.27 g (60% yield) of 1-furfuryl-2-thio-3-(2,6-xylyl)urea.

EXAMPLE 5

Evaluation of Test Compounds for Enhancing the Growth Rate and Improving Feed Efficiency in Sheep To determine the effectiveness of 1-furfuryl-2-thio-3-(2,6-xylyl)urea for increasing the growth rate and improving feed efficiency in sheep, wether lambs are randomly allocated to pens, five lambs per pen. Six pens per treatment are used. All animals are placed in their pens and held overnight without water. The following morning all lambs are weight, returned to their pens and provided with test diet offered ad libitum. Water is also offered ad libitum. At two-week intervals water is withheld from all lambs overnight. The folowing morning all lambs are weighed. During the entire test period unconsumed feed is collected and weighed back prior to the morning feeding and saved. The collected refused feed is weighed every two weeks on the day the lambs are weighed.

Six weeks after testing is initiated the trials are terminated and the lambs weighed. The average daily gain and the amount of feed consumed per unit of gain are then determined for each treatment group. Data obtained are reported in table I below.

| Diet | |
| --- | --- |
| Ingredient | % by weight |
| Soybean Oil Meal (49%) | 13 |
| Ground Yellow Corn | 30 |
| Ground Corn Cobs | 30 |
| Dehydrated Alfalfa Meal | 15 |
| Molasses | 10 |
| Iodized Salt | 0.5 |
| Dicalcium Phosphate | 1.0 |
| Pre-mix | 0.5 |
| Total | 100 |

| Pre-mix for One Ton of Feed | |
| --- | --- |
| | (grams) |
| Trace Minerals | 454 |
| Vitamin A (30,000 Iu/g) | 133 |
| Vitamin D3 (200,000 Iu/g) | 5 |
| Vitamin E (125,000 Iu/g) | 49.5 |
| Corn Oil | 100 |
| Ground Corn | 3798.5 |

TABLE I

Weight Gain and Feed Efficiency of Control and
1-Furfuryl-2-Thio-3-(2,6-xylyl)urea-Treated Wether Lambs
Six Week Data

| Treatment | ppm in diet | ADG (grams) | % Over Control | Feed/ Gain | % Improvement Over Control |
|---|---|---|---|---|---|
| Control | 0 | 204 | — | 9.73 | — |
| 1-Furfuryl-2-Thio-3-(2,6-xylyl)urea | 25 | 212 | + 3.9 | 9.00 | + 7.5 |
| " | 50 | 234 | + 14.7 | 8.76 | + 10.0 |
| " | 100 | 236 | + 15.7 | 8.80 | + 9.6 |

ADG = Average daily gain

EXAMPLE 6

Evaluation of Test Compounds as Animal Feed Additives for the Enhancement of the Growth Rate of Poultry Test Animals One day old Hubbard X Hubbard Crossbred Chicks, randomly allotted to pens of ten chicks (5 males and 5 females) each.

Procedure

Eight pens of chicks are used for unmedicated controls, and four pens of chicks are used it each level of drug. The duration of the experiment is 13 days.

The controls are offered an unmedicated diet of Broiler ration No. 453 (composition given below) and water ad libitum. Medicated chicks are offered the same diet containing the test drug at the levels indicated above, and water ad libitum. The weight of the chicks is determined at the beginning and on completion of the experiments. Weight gains and the amount of feed consumed are also determined. The thus obtained data are averaged and summarized in Table II below, wherein the percent improvement in weight gains and feed/gain ratios are given.

EXAMPLE 7

Evaluation of Test Compounds for Enhancing the Growth Rate and Improving Feed Efficiency in Swine In the following test female and castrate weanling pigs are allocated to pens, 5 pigs per pen (3 male, 2 female) per treatment. These pigs are weighed on the day the test is initiated and then they are placed in their pens. A sufficient amount of feed to last one week is added to each feeder at the start of the test and each week thereafter. Both water and feed are provided ad libitum and all pigs are weighed every other week after the trial is begun. The trial is continued for 42 days after which the pigs are weighed and the test terminated. The amount to feed consumed per pen is recorded every two weeks on the day the pigs are weighed. Data obtained are reported in table III below.

| Swine Grower Diet | |
|---|---|
| Ingredient | % |
| Corn Ground | 77.825 |
| Soybean Meal | 17.50 |
| Meat + Bone Meal | 2.50 |
| Di Calcium Phosphate | 0.75 |
| Iodized Salt | 0.50 |
| Limestone | 0.60 |
| Vitamin Premix | 0.25 |
| Mineral Premix | 0.075 |
| | 100.000 |

TABLE III

Effects of 1-Furfuryl-2-thio-3-(2,6-xylyl)urea on Weight Gain and Feed Efficiency of Weanling Pigs; A six week study

| Treatment | ppm | ADG (Grams) | % Control | F/G | % Control |
|---|---|---|---|---|---|
| Control | 0 | 779 | — | 2.87 | — |
| 1-Furfuryl-2-thio-3-(2,6-xylyl)urea | 10 | 826 | +6.0 | 2.73 | +4.9 |
| | 50 | 765 | −1.8 | 2.77 | +3.5 |

TABLE II

Effects of Test Compounds on Weight Gain and Feed Efficiency of Chicks in Thirteen Day Battery Tests

| Treatment | Dosage ppm | Weight/chick(g) start | Weight/chick(g) finish | Weight gain per chick(g) | Feed Consumed per chick(g) | F/G | % improvement over controls gain | % improvement over controls F/G |
|---|---|---|---|---|---|---|---|---|
| Control | 0 | 44.6 | 314.1 | 269.5 | 377.3 | 1.40 | — | — |
| 1-(6-ethyl-o-tolyl)-3-furfuryl-2-thiourea | 2.5 | 44.6 | 316.8 | 272.2 | 375.6 | 1.38 | + 1.0 | + 1.4 |
| 1-furfuryl-3-phenyl-thiourea | 2.5 | 44.6 | 317.9 | 273.3 | 379.9 | 1.39 | + 1.4 | + 0.8 |
| Control | 0 | 44.6 | 306.7 | 262.1 | 369.6 | 1.41 | — | — |
| 1-furfuryl-2-thio-3-(2,6-xylyl)urea | 2.5 | 44.6 | 315.1 | 270.5 | 373.3 | 1.38 | + 3.2 | + 2.0 |
| 1-furfuryl-3-mesityl-2-thiourea | 2.5 | 44.6 | 317.1 | 272.5 | 378.8 | 1.39 | + 3.9 | + 1.9 |
| 1-(2,6-diethylphenyl)-3-furfuryl-2-thiourea | 2.5 | 44.6 | 314.9 | 270.3 | 375.7 | 1.39 | + 3.1 | + 1.9 |
| 1-furfuryl-2-thio-3-o-tolylurea | 2.5 | 44.6 | 311.7 | 267.1 | 373.9 | 1.40 | + 1.9 | + 1.2 |
| Control | 0 | 38 | 263.8 | 225.8 | 338.7 | 1.51 | — | — |
| 1-(2,6-dichloro-phenyl)-3-furfuryl-2-thiourea | 2.5 | 38 | 267.2 | 229.2 | 343.3 | 1.51 | + 1.5 | — |
| 1-furfuryl-3-(o-nitrophenyl)-2-thiourea | 2.5 | 38 | 273.3 | 235.3 | 349.4 | 1.49 | + 4.2 | + 1.0 |
| 1-furfuryl-3-(o-methoxyphenyl)-2-thiourea | 2.5 | 38 | 271.4 | 233.4 | 344.4 | 1.48 | + 3.4 | + 1.9 |
| 1-furfuryl-3-(p-nitrophenyl)-2-thiourea | 2.5 | 38 | 267.3 | 229.3 | 340.1 | 1.49 | + 1.6 | + 1.0 |

TABLE III-continued

Effects of 1-Furfuryl-2-thio-3-(2,6-xylyl)urea on Weight Gain and Feed Efficiency of Weanling Pigs; A six week study

| Treatment | ppm | ADG (Grams) | % Control | F/G | % Control |
|---|---|---|---|---|---|
| | 100 | 810 | +4.0 | 2.79 | +2.8 |

We claim:

1. A method for enhancing the growth rate of an animal and increasing the efficiency of feed utilization thereby, comprising: orally or parenterally administering to said animal an effective amount of a compound having the structure:

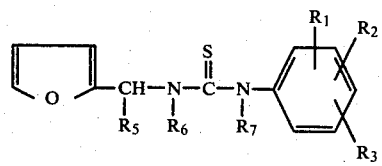

wherein $R_1$ is hydrogen, halogen, alkyl $C_1-C_4$, alkoxy $C_1-C_4$, $CF_3$, alkylthio $C_1-C_4$, nitro, cyano, $C_1-C_4$ alkanoyl —$COOR_4$ or

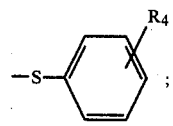

$R_2$ and $R_3$ each represent hydrogen, halogen, alkyl $C_1-C_4$ or alkoxy $C_1-C_4$; $R_4$ is hydrogen or alkyl $C_1-C_4$; $R_5$, $R_6$ and $R_7$ are each hydrogen or alkyl $C_1-C_4$.

2. The method according to claim 1 wherein $R_1$ is alkyl $C_1-C_4$; $R_2$ and $R_3$ are each hydrogen or alkyl $C_1-C_4$; $R_5$, $R_6$ and $R_7$ are each hydrogen.

3. The method according to claim 1 wherein said compound is administered to said animals in an amount equivalent to between 1 and 10,000 ppm in or with an animal feed.

4. The method according to claim 1 wherein said animals are sheep, cattle, swine, goats or poultry.

5. The method according to claim 1 wherein said compound is 1-furfuryl-2-thio-3-(2,3-xylyl)urea.

6. The method according to claim 1 wherein said compound is 1-furfuryl-2-thio-3-(2,6-xylyl)urea.

7. The method according to claim 1 wherein said compound is 1-furfuryl-3-mesityl-2-thiourea.

8. The method according to claim 1 wherein said compound is 1-(2,6-dichlorophenyl)-3-furfuryl-2-thiourea.

9. The method according to claim 1 wherein said compound is 1-(p-acetylphenyl)-3-furfurty-2-thiourea.

10. An animal feed composition comprising: an edible animal feedstuff containing from 0.0001% to 1.0% by weight of a compound having the formula:

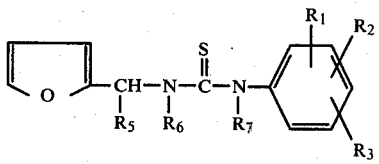

wherein $R_1$ is hydrogen, halogen, alkyl $C_1-C_4$, alkoxy $C_1-C_4$, $CF_3$, alkylthio $C_1-C_4$, nitro, cyano, $C_1-C_4$ alkanoyl, —$COOR_4$ or

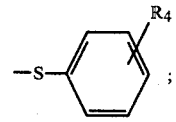

$R_2$ and $R_3$ are each hydrogen, halogen, alkyl $C_1-C_4$ or alkoxy $C_1-C_4$; $R_4$ is hydrogen or alkyl $C_1-C_4$; $R_5$, $R_6$ and $R_7$ each represent hydrogen or alkyl $C_1-C_4$.

* * * * *